(12) United States Patent
Lou (10) Patent No.: US 11,179,116 B2
(45) Date of Patent: Nov. 23, 2021

(54) CONTROLLING PULSE PILEUP (71) Applicant: Shanghai Neusoft Medical Technology Co., Ltd., Shanghai (CN)

(72) Inventor: Shanshan Lou, Shanghai (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 16/868,984

(22) Filed: May 7, 2020

(65) Prior Publication Data

US 2020/0352526 A1 Nov. 12, 2020

(30) Foreign Application Priority Data

May 7, 2019 (CN) .......................... 201910376896.6

(51) Int. Cl.
*A61B 6/03* (2006.01)
*A61B 6/00* (2006.01)
*G01T 1/17* (2006.01)

(52) U.S. Cl.
CPC ............ *A61B 6/032* (2013.01); *A61B 6/4241* (2013.01); *A61B 6/488* (2013.01); *A61B 6/544* (2013.01); *G01T 1/171* (2013.01)

(58) Field of Classification Search
CPC ....... A61B 6/032; A61B 6/4241; A61B 6/488; A61B 6/544; G01T 1/171
See application file for complete search history.

(56) References Cited

U.S. PATENT DOCUMENTS

| | | | |
|---|---|---|---|
| 2014/0233693 A1* | 8/2014 | Wang | A61B 6/5294 378/5 |
| 2014/0314211 A1* | 10/2014 | Zou | A61B 6/482 378/207 |
| 2014/0328465 A1* | 11/2014 | Herrmann | G01T 1/17 378/62 |
| 2015/0185332 A1* | 7/2015 | Herrmann | G01T 1/171 250/336.1 |
| 2015/0282778 A1* | 10/2015 | Kato | A61B 6/488 378/5 |
| 2016/0195623 A1* | 7/2016 | Wang | G01T 1/171 250/370.09 |
| 2017/0273640 A1* | 9/2017 | Danielsson | A61B 6/4241 |
| 2017/0322319 A1* | 11/2017 | Iniewski | G01T 1/171 |
| 2018/0211417 A1* | 7/2018 | Miyazaki | G06T 7/11 |
| 2020/0268330 A1* | 8/2020 | Altunbas | A61B 6/4216 |
| 2020/0323508 A1* | 10/2020 | Zhou | A61B 6/4241 |

* cited by examiner

*Primary Examiner* — Blake C Riddick
(74) *Attorney, Agent, or Firm* — Fish & Richardson P.C.

(57) ABSTRACT

Methods, devices, systems, and apparatus for controlling pulse pileup are provided. In one aspect, a method of controlling pulse pileup includes: obtaining scan protocol parameters of a computed tomography (CT) device, the scan protocol parameters including an exposure voltage, an exposure duration for each revolution of a scanning of an object, and a number of views for each revolution, determining an angle of a radioactive source for an i-th view based on the number of views and an initial position of the radioactive source, obtaining an optimal exposure current for the i-th view under the exposure voltage by minimizing an output value of an objective function for the i-th view, and determining a current view based on the exposure duration for each revolution and a current exposure moment to perform the scanning on the object with the optimal exposure current for the current view.

20 Claims, 4 Drawing Sheets

CONTROLLING PULSE PILEUP

CROSS REFERENCE TO RELATED APPLICATIONS

This application claims priority to Chinese Patent Application No. 201910376896.6 filed on May 7, 2019, the entire contents of which are incorporated herein by reference.

TECHNICAL FIELD

The present disclosure relates to the technical field of computed tomography (CT), and more particularly, to controlling pulse pileup.

BACKGROUND

A CT scanner includes a radioactive source (such as a bulb tube) and a detector. The radioactive source emits radioactive rays (such as X-rays), and the radioactive rays are attenuated by a scanned object, and then received by the detector and converted into signals that can be recognized by a computer for image reconstruction. In practical applications, the detector can be a photon-counting detector. The photon-counting detector can directly convert energy information of a single photon into a pulse signal. The pulse height corresponds to the energy of the photon of the radioactive rays, and the number of pulses corresponds to the number of photons.

Though the photon-counting detector has advantages of energy resolution, the photon-counting detector has deficiencies too in practical applications. Since the photon-counting detector requires a certain time period (i.e., a dead time) to perform pulse formation, discrimination and counting, if a time interval at which the photons are successively incident on a sub-detector of the photon-counting detector is shorter than the dead time, the sub-detector will not be able to independently identify every incident photon, and the pulse signals generated by these adjacent incident photons will be superimposed together to form pulse pileup. Pulse pileup not only causes photon counting loss, but also causes energy spectrum distortion, which is undesirable for photon counting CT. Therefore, in photon counting CT, to achieve better imaging quality, the pulse pileup should be effectively controlled.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for effectively controlling pulse pileup.

One aspect of the present disclosure features a method of controlling pulse pileup, including: obtaining scan protocol parameters of a computed tomography (CT) device, the scan protocol parameters including an exposure voltage, an exposure duration for each revolution of a scanning of an object, and a number of views for each revolution of the scanning; determining an angle of a radioactive source of the CT device for an i-th view based on the number of views for each revolution of the scanning and an initial position of the radioactive source, where i is a positive integer among a range from 1 to the number of views for each revolution of the scanning; by minimizing an output value of an objective function for the i-th view, obtaining an optimal exposure current for the i-th view under the exposure voltage, where the output value of the objective function for the i-th view is determined based on an incident photon count rate (ICR) of each sub-detector of a photon-counting detector for the i-th view, an upper limit of ICR, and a lower limit of ICR, and where the ICR of the sub-detector for the i-th view is determined based on the exposure voltage, the exposure current, an attenuation coefficient of the object, and a path length for the i-th view, the path length for the i-th view being an attenuation length of a radioactive ray travelling from the radioactive source to the sub-detector and passing through the object under the angle of the radioactive source for the i-th view; and determining a current view based on the exposure duration for each revolution of the scanning and a current exposure moment to perform the scanning on the object with the optimal exposure current for the current view.

In some embodiments, the method further includes: establishing a standard geometric model of the object, the standard geometric model being an ellipse model; and determining the attenuation length of the radioactive ray travelling from the radioactive source to the sub-detector and passing through the standard geometric model under the angle of the radioactive source for the i-th view to be the path length. The method can include: before obtaining the optimal exposure current for the i-th view under the exposure voltage, performing location scanning on the object to determine a size of the object; scaling, based on the size of the object, the standard geometric model to obtain an equivalent geometric model of the object; and determining the attenuation length of the radioactive ray travelling from the radioactive source to the sub-detector and passing through the equivalent geometric model under the angle of the radioactive source for the i-th view to be the path length.

In some embodiments, the method further includes: determining the upper limit of ICR based on a maximum value of deadtime loss rate and a dead time of the photon-counting detector. A deadtime loss rate of the sub-detector for the i-th view can be associated with the ICR of the sub-detector and an observed photon count rate (OCR) of the sub-detector for the i-th view, and the OCR of the sub-detector for the i-th view can be associated with the ICR of the sub-detector for the i-th view and the dead time of the photon-counting detector.

In some embodiments, the method further includes: determining the lower limit of ICR based on a minimum value of signal-to-noise ratio, an area of the sub-detector, and an exposure duration of the i-th view, where the exposure duration of the i-th view is obtained by dividing the exposure duration for each revolution of the scanning by the number of views for each revolution of the scanning. A signal-to-noise ratio of the sub-detector for the i-th view can be associated with the ICR of the sub-detector for the i-th view, the area of the sub-detector, and the exposure duration of the i-th view.

In some embodiments, the method includes: for each sub-detector for the i-th view, determining an increment of the output value of the objective function for the i-th view based on a relationship between the ICR of the sub-detector and the upper limit of ICR and the lower limit of ICR. When the ICR of the sub-detector is greater than the upper limit of ICR, the output value of the objective function for the i-th view can be increased from an initial output value by the increment that is based on a difference between the ICR of the sub-detector and the upper limit of ICR. When the ICR of the sub-detector is less than the lower limit of ICR, the output value of the objective function for the i-th view can be increased by the increment that is based on a difference the ICR of the sub-detector and the lower limit of ICR. When the ICR of the sub-detector is between the lower limit of ICR and the upper limit of ICR, the increment of the output value of the objective function can be substantially identical to zero or within a predetermined range, the increment being based on a difference the ICR of the sub-detector and the upper limit of ICR and the lower limit of ICR.

In some embodiments, determining the optimal exposure current for the i-th view under the exposure voltage includes: determining, based on the exposure voltage and a plurality of exposure currents, a plurality of sets of ICR for the i-th view, each of the plurality of sets of ICR including a respective ICR of each sub-detector under a respective exposure current corresponding to the set of ICR; for each of the plurality of sets of ICR, obtaining an output value of the objective function for the set of ICR based on the respective ICR of each sub-detector in the set of ICR, the lower limit of ICR, and the upper limit of ICR; identifying a minimum output value of the objective function from the obtained output values of the objective function for the plurality of sets of ICR; and determining an exposure current for the minimum output value of the objective function as the optimal exposure current for the i-th view under the exposure voltage.

In some embodiments, the photon-counting detector includes a Non-paralyzable photon-counting detector.

Another aspect of the present disclosure features a device including: at least one processor; and at least one non-transitory machine readable storage medium coupled to the at least one processor having machine-executable instructions stored thereon that, when executed by the at least one processor, cause the at least one processor to perform operations including: obtaining scan protocol parameters of a computed tomography (CT) device, the scan protocol parameters including an exposure voltage, an exposure duration for each revolution of a scanning of an object, and a number of views for each revolution of the scanning; determining an angle of a radioactive source of the CT device for an i-th view based on the number of views for each revolution of the scanning and an initial position of the radioactive source, where i is a positive integer in a range from 1 to the number of views for each revolution of the scanning; by minimizing an output value of an objective function for the i-th view, obtaining an optimal exposure current for the i-th view under the exposure voltage, where the output value of the objective function for the i-th view is determined based on an incident photon count rate (ICR) of each sub-detector of a photon-counting detector for the i-th view, an upper limit of ICR, and a lower limit of ICR, and where the ICR of the sub-detector for the i-th view is determined by the exposure voltage, the exposure current, an attenuation coefficient of the object, and a path length for the i-th view, the path length for the i-th view being an attenuation length of a radioactive ray travelling from the radioactive source to the sub-detector and passing through the object under the angle of the radioactive source for the i-th view; and determining a current view based on the exposure duration for each revolution of the scanning and a current exposure moment to perform the scanning on the object with the optimal exposure current for the current view.

In some embodiments, the operations further include: establishing a standard geometric model of the object, the standard geometric model being an ellipse model; and determining the attenuation length of the radioactive ray travelling from the radioactive source to the sub-detector and passing through the standard geometric model under the angle of the radioactive source for the i-th view to be the path length. The operations can include: before obtaining the optimal exposure current for the i-th view under the exposure voltage, performing location scanning on the object to determine a size of the object; scaling, based on the size of the object, the standard geometric model to obtain an equivalent geometric model of the object; and determining the attenuation length of the radioactive ray travelling from the radioactive source to the sub-detector and passing through the equivalent geometric model under the angle of the radioactive source for the i-th view to be the path length.

In some embodiments, the operations further include: determining the upper limit of ICR based on a maximum value of deadtime loss rate and a dead time of the photon-counting detector. A deadtime loss rate of the sub-detector for the i-th view can be associated with the ICR of the sub-detector and an observed photon count rate (OCR) of the sub-detector for the i-th view, and the OCR of the sub-detector for the i-th view can be associated with the ICR of the sub-detector for the i-th view and the dead time of the photon-counting detector.

In some embodiments, the operations further include: determining the lower limit of ICR based on a minimum value of signal-to-noise ratio, an area of the sub-detector, and an exposure duration of the i-th view, where the exposure duration of the i-th view is obtained by dividing the exposure duration for each revolution by the number of views for each revolution. A signal-to-noise ratio of the sub-detector for the i-th view can be associated with the ICR of the sub-detector for the i-th view, the area of the sub-detector and the exposure duration of the i-th view.

In some embodiments, the operations include: for each sub-detector for the i-th view, determining an increment of the output value of the objective function for the i-th view based on a relationship between the ICR of the sub-detector and the upper limit of ICR and the lower limit of ICR. When the ICR of the sub-detector is greater than the upper limit of ICR, the output value of the objective function for the i-th view can be increased from an initial output value by the increment that is based on a difference between the ICR of the sub-detector and the upper limit of ICR. When the ICR of the sub-detector is less than the lower limit of ICR, the output value of the objective function for the i-th view can be increased from an initial value by the increment that is based on a difference the ICR of the sub-detector and the lower limit of ICR. When the ICR of the sub-detector is between the lower limit of ICR and the upper limit of ICR, the increment of the output value of the objective function can be substantially identical to zero or within a predetermined range, the increment being based on a difference the ICR of the sub-detector and the upper limit of ICR and the lower limit of ICR.

In some embodiments, the operations include: determining, based on the exposure voltage and a plurality of exposure currents, a plurality of sets of ICR for the i-th view, each of the plurality of sets of ICR including an ICR of each sub-detector under a respective exposure current corresponding to the set of ICR; for each of the plurality of sets of ICR, obtaining, based on the ICR of each sub-detector in the set of ICR, the lower limit of ICR and the upper limit of ICR, an output value of the objective function for the set of ICR; identifying a minimum output value of the objective function from the obtained output values of the objective function for the plurality of sets of ICR; and determining an exposure current for the minimum output value of the objective function as the optimal exposure current for the i-th view under the exposure voltage.

In some embodiments, the photon-counting detector includes a Non-paralyzable photon-counting detector.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Three methods may be employed to control pulse pileup. First, a tube voltage and a tube current can be reduced. For example, by appropriately reducing the exposure voltage and current, the photon count rate can be suppressed at the radioactive ray emitting end, thereby reducing the number of photons eventually incident on the sub-detector of the detector per unit time. Second, the incident photons can be filtered with an appropriate filter. The radioactive beam can be attenuated after passing through the filter, and the photon count rate incident on the sub-detector can be reduced, thereby reducing the pulse pileup. Third, the size of each sub-detector in the photon-counting detector can be reduced. By reducing the size of the sub-detectors, the number of photons incident on each sub-detector can be reduced at the same exposure level, thereby increasing an average time interval between incident photons and reducing the pulse pileup. Although the above three methods may control the pulse pileup to a certain level, during a scanning process, with change in scanning position and view angle, the ray attenuation length continuously changes, and none of the above three methods can adaptively control in real time the pulse pileup level at each scanning position and each view angle and therefore the above three methods have a limited scope of application.

In view of the above, implementations of the present disclosure provide methods of controlling pulse pileup. Before scanning, scan protocol parameters can be first obtained, and an optimal exposure current for each view in each revolution of scanning can be determined based on the scan protocol parameters and an objective function. When scanning, a current view can be determined based on the exposure duration of each revolution of scanning and the current exposure moment. That is, based on real-time change in the view angle, the pulse pileup can be adaptively controlled at an optimal level with an optimal exposure current for the current view angle.

To facilitate understanding of the technical solution of controlling the pulse pileup provided by examples of the present disclosure, the technical terms involved in the present disclosure will be described below in conjunction with the accompanying drawings.

Figure 1:
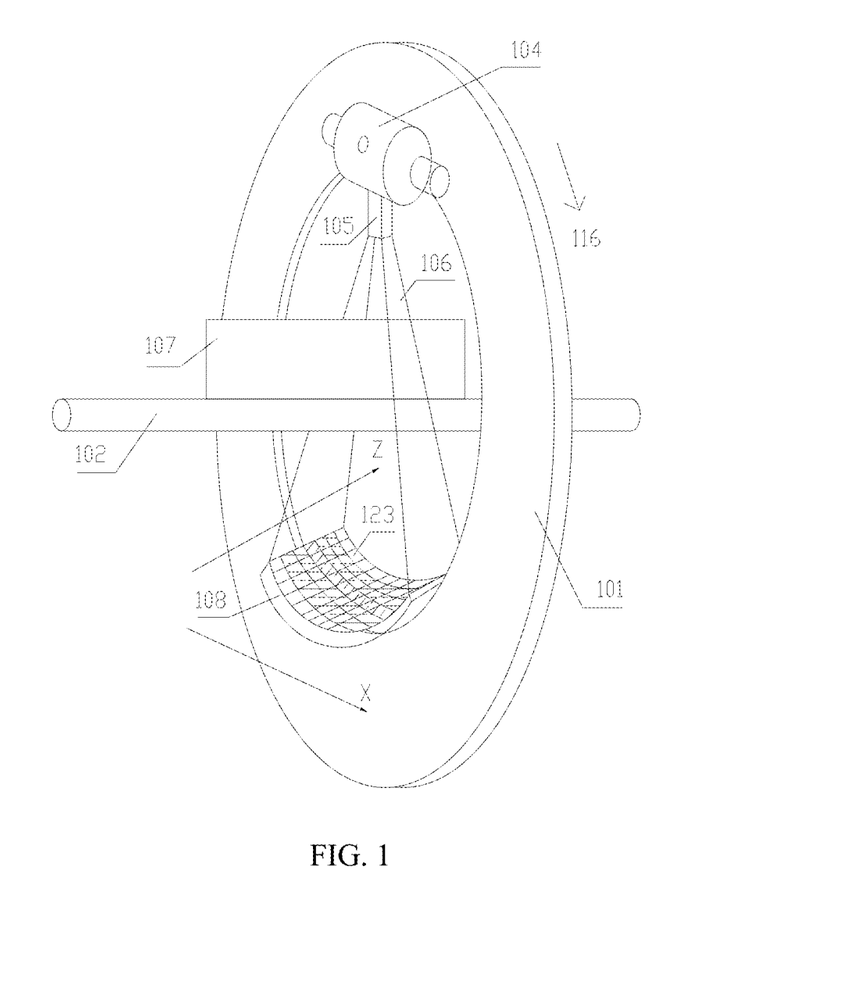
FIG. 1 is a schematic diagram of a scanning device according to one or more examples of the present disclosure.

FIG. 1 is a schematic diagram of a CT device according to one or more examples of the present disclosure. The CT device includes a cone beam CT scanner or a fan beam CT scanner, which is not limited herein.

The scanner includes a support 101 rotatable about a rotation axis 102. The support 101 can be driven by a motor (not shown in the FIG. 1).

A radioactive source 104 can be an X-ray source, and can form a cone-shaped radioactive beam 106 through an aperture 105. The cone-shaped radioactive beam 106 can pass through an object 107 at the central position of the support 101 and hit into a photon-counting detector 108. The photon-counting detector 108 is arranged on the support 101 at a position opposite to the radioactive source 104, such that the surface of the photon-counting detector 108 is covered by the cone-shaped radioactive beam 106.

During the scanning of the object 107, the radioactive source 104, the aperture 105, and the photon-counting detector 108 are rotated along the support 101 in a direction indicated by an arrow 116. When applied to the medical field, the object 107 can be a patient, and the patient moves in parallel along the direction of the rotation axis 102. At the same time, the support 101 can also rotate to scan the patient along a spiral scanning path.

The photon-counting detector 108 includes n rows and m columns of sub-detectors, and is configured to receive rays attenuated by the object 107. For example, a numeral reference 123 in FIG. 1 denotes a sub-detector located in the third row and the seventh column. The scanning of the object 107 can include a number of revolutions. Each revolution of the scanning represents a respective part of the scanning during a respective time period with a respective exposure duration. Each revolution can correspond to a number of views. When the radioactive source 104 rotates 360 degrees, it can be considered that one revolution of the scanning is completed.

Through the above description, the working principle of the CT scanner can be clearly understood. Based on the above, the technical solution provided by the present disclosure will be described. The implementation of the technical solution provided by the present disclosure can include three parts: the first is to determine of system response curves, the second is to establish a standard control model, and the third is to perform real-time scanning and control, which will be described one by one below.

I. Determination of System Response Curves

In some examples, the system response curves include the following three curves.

1. The first curve can be a response curve representing a relationship between an Emitted Count Rate (ECR) of a radioactive source and an exposure voltage and an exposure current. The ECR of the radioactive source is defined as: under a vacuum (or air) scanning condition (that is, without a scanned object), the number of photons incident on a sub-detector per unit time, that is, the number of photons incident on the sub-detector per unit time when no object is scanned. The response curve can be expressed as the following formula:

$$ECR = F(V, I, d) \quad (1)$$

where, V denotes an exposure voltage, I denotes an exposure current, d denotes a distance from the radioactive source to the sub-detector, and F denotes a function relationship between ECR and V, I, and d.

2. The second curve can be a response curve representing a relationship between an incident photon count rate (ICR) and an ECR of a sub-detector. The ICR is defined as the number of photons that enter the sub-detector per unit time after the radioactive rays are attenuated by the scanned object. The response curve can be expressed as the following formula:

$$ICR = g(ECR; I, \mu, L) \quad (2)$$

where I denotes an exposure current, $\mu$ denotes an attenuation coefficient of a scanned object, L denotes a path length of rays passing through the scanned object under an angle of the radioactive source for a current view, and g denotes a function relationship between ICR and ECR, I and L.

3. The third curve can be a response curve representing a relationship between an observed photon count rate (OCR), the incident photon count rate ICR and a dead time of a sub-detector. The response curve can be expressed as the following formula:

$$OCR = h(ICR, T_D) \quad (3)$$

where ICR denotes an incident photon count rate, $T_D$ denotes a dead time, h denotes a function relationship between OCR and ICR and $T_D$.

II. Establishment of a Standard Control Model

The establishment of a standard control model can include the following two aspects.

1. Establishing a standard geometric model of an object to be scanned. When the object to be scanned is a person, an ellipse model (with a semi-major axis a and a semi-minor axis b) in a two-dimensional coordinate system (x, y) can be established for any longitudinal section of the human body. The standard geometric model of the longitudinal section can be expressed as the following formula:

$$\frac{x^2}{a^2} + \frac{y^2}{b^2} = 1 \quad (4)$$

2. Constructing an objective function. The construction of the objective function takes two factors into consideration. On the one hand, the pulse pileup depends on ICR. Therefore, the ICR of the sub-detector is to be controlled to a certain level to ensure that the photon counting loss and spectral distortion caused by pulse pileup are within acceptable ranges, that is, an upper limit of ICR can be determined. On the other hand, it may be necessary to ensure that each sub-detector receives enough photons to ensure a certain signal-to-noise ratio, that is, a lower limit of ICR can be determined. ICR of each sub-detector can be controlled between the upper limit and the lower limit, and thus the objective function can be expressed as the following formula:

$$z = f(\overrightarrow{ICR}; ICR_{min}, ICR_{max}) \quad (5)$$

where z denotes an output value of the objective function, $\overrightarrow{ICR}$ denotes a vector composed of the ICR of each sub-detector, $\overrightarrow{ICR} = [ICR[1], ICR[2], ICR[3], \ldots, ICR[N]]$, where ICR [1] denotes the ICR of the first detector sub-detector, ICR [2] denotes the ICR of the second sub-detector, and ICR [3] denotes the ICR of the third sub-detector count rate, ICR [N] denotes the ICR of the N-th sub-detector, and N is the total number of sub-detectors in the photon-counting detector. $ICR_{min}$ denotes the lower limit of ICR. $ICR_{max}$ denotes the upper limit of ICR. An output value of the objective function can be increased from an initial output value or remain unchanged (or within a predetermined range) based on a relationship between the ICR of each sub-detector, $ICR_{min}$ and $ICR_{max}$. In practical applications, ICR of each sub-detector can be kept greater than or equal to $ICR_{min}$ and less than or equal to $ICR_{max}$.

When constructing the objective function, the condition to be satisfied can include: when the ICR of the sub-detector is greater than $ICR_{max}$, the larger a difference between the ICR of the sub-detector and $ICR_{max}$ is, the more an increment of an output value of the objective function can be; when the ICR of the sub-detector is less than $ICR_{min}$, the larger a difference between the ICR of the sub-detector and $ICR_{min}$ is, the more an increment of an output value of the objective function can be; and when the ICR of the sub-detector is between $ICR_{min}$ and $ICR_{max}$, the output value of the objective function does not change substantially or the increment of the output value of the objective function can be relatively less. In examples of the present disclosure, the objective function can be constructed in any manner as long as the condition is satisfied.

Here, $ICR_{min}$ can be related to the noise of the CT device, and through experiments, the relationship between a signal-to-noise ratio (SNR) and ICR can be expressed as the following formula:

$$SNR = H(ICR; A_{pixel}, T_{view}) \quad (8)$$

where $A_{pixel}$ denotes an area of a sub-detector, $T_{view}$ denotes a scanning time of a view, H denotes a function relationship between SNR and ICR, $A_{pixel}, T_{view}$. If SNR is required to be greater than or equal to $\alpha$, that is, $SNR \geq \alpha$, the following formula can be obtained:

$$ICR_{min} = H^{-1}(\alpha; A_{pixel}, T_{view}) \quad (7)$$

where $H^{-1}$ is an inverse function of H, which refers to an inverse function of variables ICR and SNR with $A_{pixel}$ and $T_{view}$ as parameters.

$ICR_{max}$ can be related to a Deadtime Loss Rate (DLR), DLR can be related to ICR and OCR, and OCR can be related to ICR and $T_D$. Therefore, a relationship between DLR and ICR and OCR can be represented by the following formula:

$$DLR = \frac{ICR - OCR}{ICR} = 1 - \frac{h(ICR, T_D)}{ICR} \quad (8)$$

Formula (8) can be further expressed as the following formula:

$$DLR = G(ICR, T_D) \quad (9)$$

If DLR is required to be less than or equal to β, that is, DLR≤β, the following formula can be obtained:

$$ICR\ max = G^{-1}(\beta, T_D) \quad (10)$$

where $G^{-1}$ is an inverse function of G, which refers to an inverse function of variables ICR and DLR with $T_D$ as a parameter.

Based on the above description, the method of controlling pulse pileup provided by examples of the present disclosure will be described below with reference to the accompanying drawings.

Figure 2:
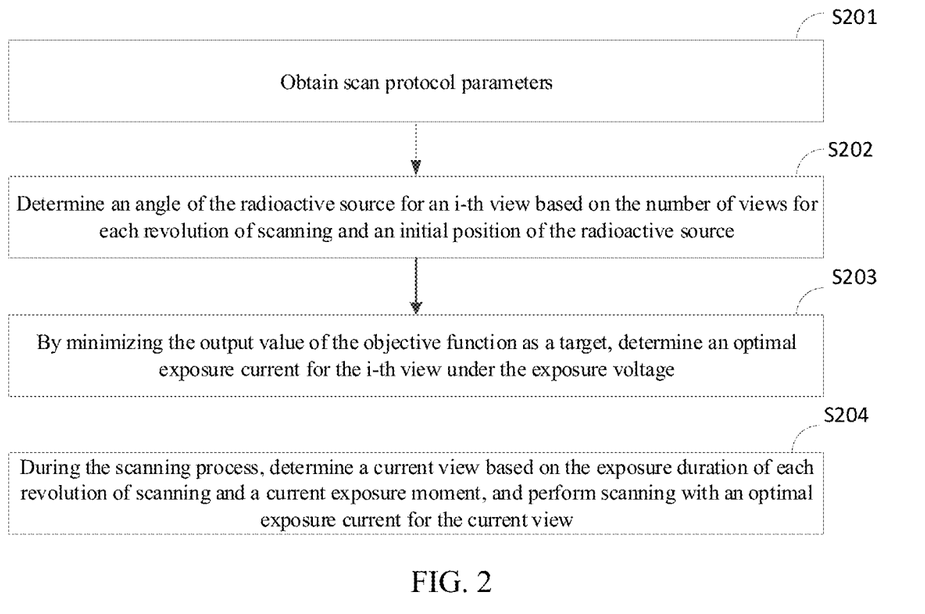
FIG. 2 is a flowchart of a process of a method of controlling pulse pileup according to one or more examples of the present disclosure.

FIG. 2 is a flowchart of a process of a method of controlling pulse pileup according to one or more examples of the present disclosure. As shown in FIG. 2, the process can include the following steps.

At S201, scan protocol parameters are obtained. The scan protocol parameters can include an exposure voltage, an exposure duration for each revolution of scanning, and the number of views for each revolution of scanning.

In some examples, the scan protocol parameters are first obtained. The scan protocol parameters can be predetermined, which includes an exposure voltage, an exposure duration for each revolution of scanning, and the number of views for each revolution of scanning.

In some examples, the exposure voltage for scanning, the exposure duration for each revolution of scanning, and the number of views for each revolution of scanning can be predetermined. Under the condition that the scan protocol parameters are known, step S202 is performed based on the scan protocol parameters.

At S202, an angle of the radioactive source for an i-th view is determined based on the number of views for each revolution of scanning and an initial position of the radioactive source.

Figure 3:
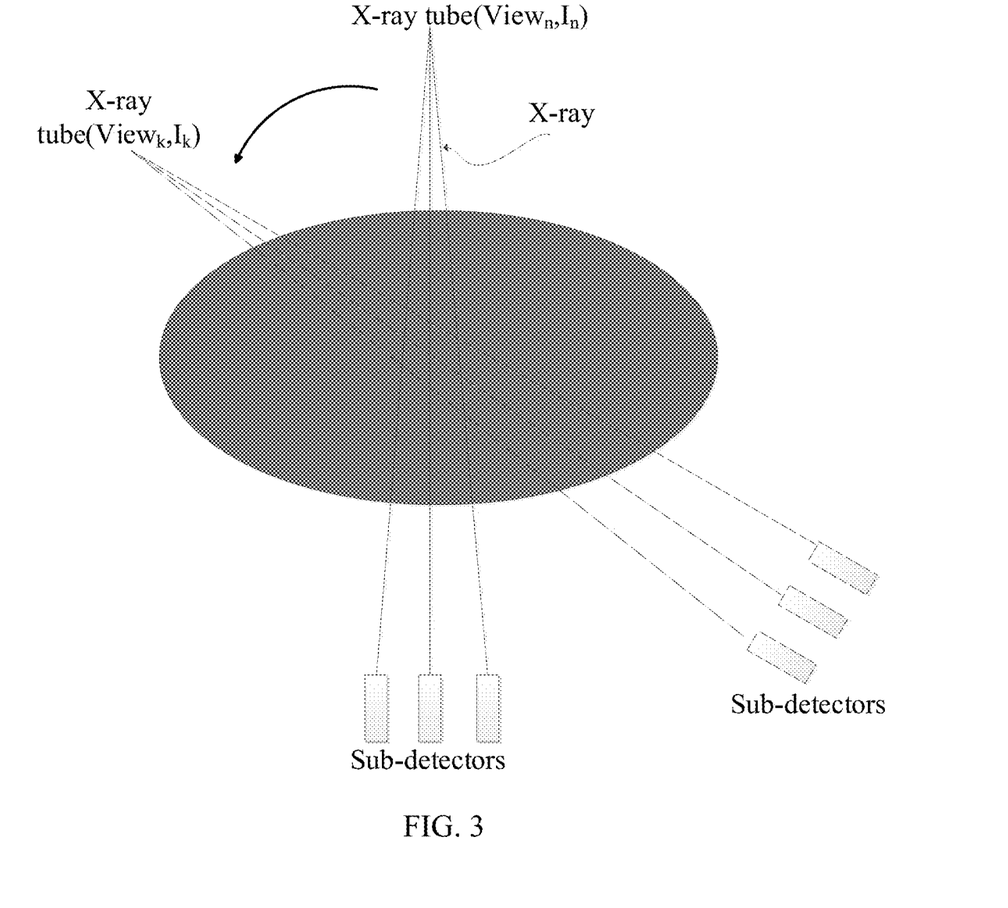
FIG. 3 is a schematic diagram of radioactive source scanning according to one or more examples of the present disclosure.

In some examples, when the number of views for each revolution of scanning and the initial position of the radioactive source are known, the angle of the radioactive source for each view can be determined. Referring to the example of the scanning of the radioactive source shown in FIG. 3, the angle of the radioactive source when the radioactive source is located directly above can be determined as the initial position, and as rotation to the left, the angle increases gradually. For example, if the angle for each revolution of scanning is 360 degrees and the number of views for each revolution of scanning is 180, the angle of the radioactive source for each view is 2 degrees. That is, the angle of the radioactive source for the first view is 2 degrees, the angle of the radioactive source for the second view is 4 degrees, the angle of the radioactive source for the third view is 6 degrees, and so forth so on.

Similarly, under the case that the exposure duration for each revolution of scanning and the number of views for each revolution of scanning are determined, an exposure duration for the i-th view can also be determined, that is, an exposure duration for each view can also be determined. For example, if the exposure duration for each revolution of scanning is 36 seconds and the number of views for each revolution of scanning is 180, the exposure duration for each view is 0.2 second. That is, the exposure duration for the first view is 0 second to 0.2 second; the exposure duration for the second view is 0.2 second to 0.4 second; and the exposure duration for the third view is 0.4 second to 0.6 second, and so on.

At S203, by minimizing the output value of the objective function as a target, an optimal exposure current for the i-th view under the exposure voltage is determined, where i is a positive integer from 1 to the number of views for each revolution of scanning.

In some examples, by minimizing the output value of the objective function as a target, an optimal exposure current for each view under the exposure voltage is determined, such that pulse pileup can be controlled in real time during the scanning process. For example, if the number of views for each revolution of scanning is 180, a total of 180 optimal exposure currents can be obtained.

Here, to determine the optimal exposure current for the i-th view, the output value of the objective function for the i-th view is determined by ICR of each sub-detector of the photon-counting detector for the i-th view, $ICR_{min}$ and $ICR_{max}$. The objective function for the i-th view satisfies the following conditions: for each sub-detector, when the ICR of the j-th sub-detector for the i-th view is greater than $ICR_{max}$, the larger a difference between the ICR of the j-th sub-detector and $ICR_{max}$ is, the more an increment of an output value of the objective function can be; when the ICR of the j-th sub-detector is less than $ICR_{min}$, the larger a difference between the ICR of the j-th sub-detector and $ICR_{min}$ is, the more the increment of the output value of the objective function can be; and when the ICR of the j-th sub-detector for the i-th view is between $ICR_{min}$ and $ICR_{max}$, that is, ICRmin<<the ICR of the j-th sub-detector≤$ICR_{max}$, the output value of the objective function substantially can remain unchanged or the increment of the output value of the objective function can be within a predetermined range, where j is a positive integer, and the value of j is in a range of 1 to the number of the sub-detectors.

It can be known from the above that the objective function for a view is related to ICR of each sub-detector for the view, $ICR_{min}$ and $ICR_{max}$. The ICR of the j-th sub-detector for the view is determined by the exposure voltage, an exposure current, an attenuation coefficient of the scanned object and a path length, where the path length is an attenuation length of radioactive rays travelling from the radioactive source to the j-th sub-detector and passing through the scanned object under the angle of the radioactive source for the view. In a specific implementation, the ICR of each sub-detector for the view can be determined using formula (2).

After the ICR of each sub-detector for the view has been determined, the relationship between each ICR and $ICR_{max}$, $ICR_{min}$ is determined. If ICR[1] of the first sub-detector is greater than $ICR_{max}$ or less than $ICR_{min}$, the output value of the objective function increases by a relatively large number. In this case, the increment of the output value of the objective function is more. If ICR[2] of the second sub-detector is greater than $ICR_{max}$ or less than $ICR_{min}$, the output value of the objective function increases again by a relatively large number. If ICR[3] of the third sub-detector is between $ICR_{min}$ and $ICR_{max}$, the output value of the objective function substantially remains unchanged or increases within a predetermined range, which can be a relatively small value, and so on so forth, to obtain the output value of the objective function for the view. By adjusting the exposure current, different output values of the objective function for the view can be obtained. By minimizing the output value of the objective function as a target, the optimal exposure current for the view can be obtained.

In some examples, the increment of the output value of the objective function can be determined based on the actual situation. For example, when ICR of the sub-detector is less than $ICR_{min}$, the increment is represented as $\Delta = w_0 *(ICR-$ $ICR_{min})^2$; when ICR of the sub-detector is greater than $ICR_{max}$, the increment is represented as $\Delta=w_1*(ICR-ICR_{max})^2$; when ICR of the sub-detector is between $ICR_{min}$ and $ICR_{max}$, the increment is represented as $\Delta=w_2*[(ICR-ICR_{min})^2+(ICR-ICR_{max})^2]$, where $w_0$, $w_1$, $w_2$ can be determined based on the actual situation, e.g., $w_0=w_1=0.5$, $w_2=0$. The larger a difference between ICR of the sub-detector greater than $ICR_{max}$ and $ICR_{max}$ or the larger a difference between ICR of the sub-detector less than $ICR_{min}$ and $ICR_{min}$ is, the more the increment for the objective function can be. When ICR of the sub-detector is between $ICR_{min}$ and $ICR_{max}$, the output value of the objective function substantially remains unchanged or increases within a predetermined range.

Here, $ICR_{max}$ is determined by the maximum value of DLR and $T_D$, and $ICR_{min}$ is determined by the minimum value of signal-to-noise ratio, an area of the sub-detector, and an exposure duration of a single view. The exposure duration of a single view is determined by the exposure duration for each revolution of scanning divided by the number of views for each revolution of scanning. In a specific implementation, $ICR_{max}$ can be determined based on formula (10), and $ICR_{min}$ can be determined based on formula (7).

In practical applications, as long as the above requirements are met, the objective function may be constructed based on actual needs. How to determine the optimal exposure current for the i-th view will be described in implementations below.

At S204, during the scanning process, a current view is determined based on the exposure duration of each revolution of scanning and a current exposure moment, and scanning is performed with an optimal exposure current for the current view.

In some examples, after the optimal exposure current for each view has been determined, in the actual scanning process, a current view can be determined based on the exposure duration of each revolution of scanning and a current exposure moment. Then, scanning is performed with an optimal exposure current for the current view, such that the exposure current can be controlled in real time, and thus the pulse pileup of each view is controlled at the optimal level.

In some examples, the current view can be determined based on the exposure duration of each revolution of scanning and the current exposure moment. For example, the exposure duration for each revolution of scanning is 36 seconds, and the current exposure moment is the 0.7th second. When the number of views for each revolution of scanning is 180, and the exposure duration for each view is 0.2 second, the current view can be determined to be the fourth view. Then, the optimal exposure current for the fourth view can be obtained, and the optimal exposure current can be used to control the radioactive source to emit radioactive rays.

In examples of the present disclosure, scan protocol parameters are obtained, and the scan protocol parameters includes an exposure voltage for scanning, an exposure duration for each revolution of scanning, and the number of views for each revolution of scanning. An angle of the radioactive source for each view is determined based on the number of views for each revolution of scanning and an initial position of the radioactive source. Then, by minimizing the output value of the objective function as a target, an optimal exposure current for each view under the exposure voltage is determined. During actual scanning, a current view can be determined in real time based on the exposure duration of each revolution of scanning and the current exposure moment, and then scanning can be performed with the optimal exposure current for the current view. That is, through the technical solutions provided by examples of the present disclosure, the exposure current can be controlled based on the real-time changes of the view position and the view angle, ICR of the sub-detector can be controlled in real time, and then the pulse pileup of the photon-counting detector during each view can be controlled within a certain range to optimize imaging quality.

According to the above description, ICR of the sub-detector can be related to the path length, and the path length can be an attenuation length of radioactive rays travelling from the radioactive source to the sub-detector and passing through a scanned object under an angle of the radioactive source for the current view. To determine the path length, in some examples, a standard geometric model is established, a longitudinal section of the standard geometric model is an ellipse, and then the attenuation length of radioactive rays travelling from the radioactive source to the j-th sub-detector and passing through the standard geometric model under the angle of the radioactive source for the i-th view is determined, as the path length.

In some examples, the longitudinal section of the established standard geometric model can be as shown in formula (4). When determining an angle of the radioactive source for the i-th view, intersection points between a radioactive ray from the radioactive source to the j-th sub-detector under the angle of the radioactive source and the standard geometric model can be determined, and a distance between the two intersection points can be determined as a path length. In an example, the radioactive ray from the radioactive source to the j-th sub-detector refers to a central ray in a beam emitted by the radioactive source.

In practical applications, different standard geometric models, such as an elliptic cylinder model and an ellipsoid model, can be established based on the scanned object.

In some examples, due to different scanned objects, during actual scanning, an equivalent geometric model can also be established based on the scanned object to determine the actual path length with the equivalent geometric model. In some examples, before determining the optimal exposure current for the i-th view under the exposure voltage, location scanning is performed on the scanned object to determine the size of the scanned object; based on the size of the scanned object, the standard geometric model can be scaled to obtain an equivalent geometric model of the scanned object. Obtaining the path length can include: determining an attenuation length of a radioactive ray travelling from the radioactive source to the j-th sub-detector and passing through the equivalent geometric model under the angle of the radioactive source for the i-th view, as the path length.

In some examples, through location scanning, the scanning position and scanning range are obtained to determine the size of the scanned object. Based on the size of the scanned object, the major axis and the minor axis of the longitudinal section of the scanned object are determined. The standard geometric model is scaled to obtain the equivalent geometric model of the scanned object. The attenuation length of a radioactive ray travelling from the radioactive source to the j-th sub-detector and passing through the equivalent geometric model under the angle of the radioactive source for the i-th view is determined as the path length. When performing location scanning, the dose of the radiation is very low. After determining the optimal exposure current for each view under the exposure voltage, scanning for diagnosis is performed on the scanned object with the optimal exposure current for the current view.

Examples of the present disclosure further provides a method of obtaining an optimal exposure current for each view, and the method will be described below with reference to the drawings.

Figure 4:
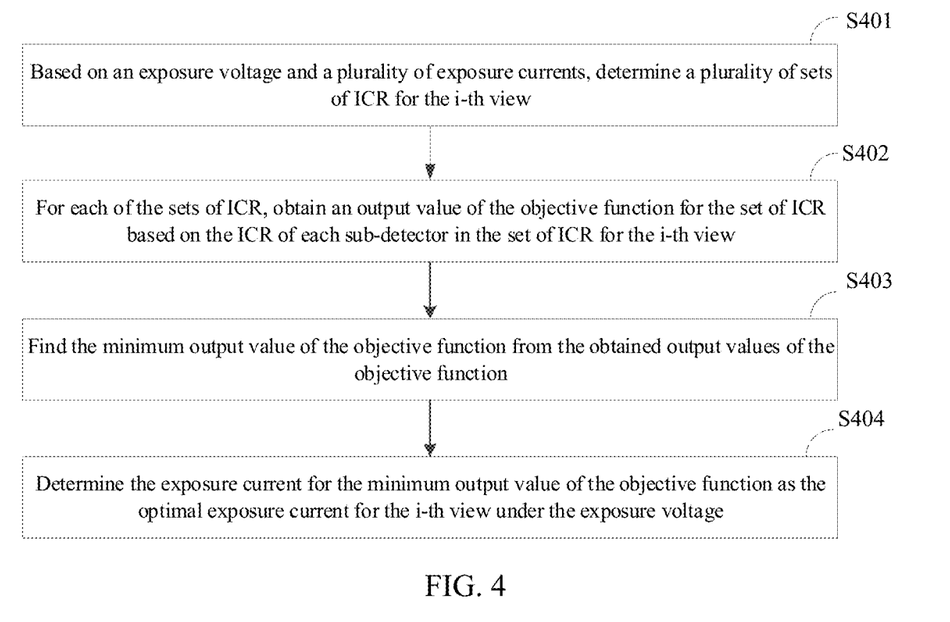
FIG. 4 is a flowchart of a process of a method of obtaining an optimal exposure current according to one or more examples of the present disclosure.

FIG. 4 is a flowchart of a process of a method of obtaining an optimal exposure current according to one or more examples of the present disclosure. As shown in FIG. 4, the process includes the following steps.

At S401, based on an exposure voltage and a plurality of exposure currents, a plurality of sets of ICR for the i-th view are determined. For each of the plurality of sets of ICR, the set of ICR includes an ICR of each sub-detector under a respective exposure current corresponding to the set of ICR.

In some examples, the exposure voltage is a determined value, the exposure current is a variable, and possible exposure currents are traversed to obtain the plurality of sets of ICR.

For ease of understanding, taking one view for each revolution of scanning as an example, a photon-counting detector includes, for example, 15 sub-detectors. When the exposure current is 0.1 mA, a first set of $ICR_{0.1}[1]$, $ICR_{0.1}[2]$, $ICR_{0.1}[3]$, ..., $ICR_{0.1}[15]$ for this view can be determined based on formula (1) and formula (2); when the exposure current is 0.2 mA, a second set of $ICR_{0.2}[1]$, $ICR_{0.2}[2]$, $ICR_{0.2}[3]$, ..., $ICR_{0.2}[15]$ for this view can be determined based on formula (1) and formula (2); when the exposure current is 0.3 mA, a third set of $ICR_{0.3}[1]$, $ICR_{0.3}[2]$, $ICR_{0.3}[3]$, ..., $ICR_{0.3}[15]$ for this view can be determined based on formula (1) and formula (2), and so on, to traverse all possible exposure currents to obtain the plurality of sets of ICR.

At S402, for each of the sets of ICR, an output value of the objective function for the set of ICR is obtained based on the ICR of each sub-detector in the set of ICR for the i-th view.

In some examples, when the plurality of sets of ICR for the i-th view are obtained, an output value of the objective function for the set of ICR is obtained based on the ICR of each sub-detector in the set of ICR, thereby obtaining the output values of the objective function for the plurality of sets of ICR.

In some examples, the objective function is constructed based on formula (5), and the output value of the objective function for each set of ICR can be determined using the constructed objective function. For example, ICRs in the first set of ICR are substituted into the constructed objective function to obtain an output value z1; ICRs in the second set of ICRs are substituted into the constructed objective function to obtain an output value z2; ICRs in the third set of ICRs are substituted into the constructed objective function, to obtain an output value z3.

At S403, the minimum output value of the objective function is found from the obtained output values of the objective function.

In some examples, after the output value of the objective function for each set of ICR is obtained through S402, the minimum value is found from the output values of the objective function for the plurality of sets. For example, three output values z1, z2, z3 of the objective function are obtained, and the minimum value is found from the three output values of the objective function.

At S404, the exposure current for the minimum output value of the objective function is determined as the optimal exposure current for the i-th view under the exposure voltage.

In some examples, after determining the minimum output value of the objective function for the i-th view, the exposure current for the minimum value is determined as the optimal exposure current for the i-th view under the exposure voltage. During scanning, when the radioactive source is running under the i-th view, the optimal exposure current is used to perform scanning. For example, if the minimum value for the i-th view is z2, then the exposure current 0.2 mA for z2 is determined as the optimal exposure current for the i-th view.

For each view for each revolution of scanning, the optimal exposure current for each view can be obtained through the above method of obtaining an optimal exposure current. The above examples use an exhaustive method to obtain the optimal exposure current for each view. In other examples, other mathematical methods such as a golden section method and a parabolic method can also be used to obtain the optimal exposure current for each view. The present disclosure is not limited herein.

Through the method of obtaining an optimal exposure current provided by examples of the present disclosure, the optimal exposure current for each view in each revolution of scanning can be determined. During actual scanning, the optimal exposure current for the current view can be obtained in real time based on the current scanning moment or scanning angle. The scanning is then performed with the optimal exposure current to control pulse pileup at an optimal level in real time and thus imaging quality of the CT device is improved.

For ease of understanding, in the following, a Non-paralyzable type photon-counting detector is used as an example to illustrate an implementation of controlling pulse pileup. For the Non-paralyzable type photon-counting detector, after a photon is incident on a sub-detector, regardless of whether pulse pileup occurs, and the signal acquisition time is a fixed dead time $T_D$.

I: Determination of System Response Relationship (1) The response curve ECR=F (V, I, d) between ECR and the exposure voltage V, exposure current I and d is determined. When the exposure voltage V is constant, ECR is proportional to the tube current I, and thus the following formula can be derived:

$$ECR = I * ECR_0(V, d) \quad (11)$$

where $ECR_0(V, d)$ denotes the number of incident photons of a single sub-detector under the exposure current of 1 mAs when the exposure voltage is V and the distance from the radioactive source to the sub-detector is d. Therefore, under vacuum (or approximate air scanning), relatively lower exposure current is used for exposure measurement (to ensure that the pulse pileup is almost negligible) to obtain $ECR_0$ under different tube voltages. In the present disclosure, the term "tube voltage" and the term "exposure voltage" can be interchangeably used; and the term "tube current" and the term "exposure current" can be interchangeably used.

(2) A response curve between OCR, ICR and $T_D$ of the sub-detector can be obtained based on a theoretical relationship of the Non-paralyzable photon-counting detector, which is expressed as the following formula:

$$OCR = \frac{ICR}{1 + ICR * T_D} \quad (12)$$

II: Establishment of a Standard Control Model (1) A standard geometric model is established. If the scanned target object is a person, an ellipse model (with a semi-major axis $a_0$ and a semi-minor axis $b_0$) can be established for any tomographic cross-section of the human body, then the standard geometric model of the tomographic cross-section can be expressed as:

$$\frac{x^2}{a_0^2} + \frac{y^2}{b_0^2} = 1 \tag{13}$$

(2) The path length is determined. An equivalent geometric model is determined based on the standard geometric model (13), and an attenuation length $L_{ij}$ of the j-th sub-detector under the i-th view is determined as the path length.

(3) A control standard and an objective function are constructed. The construction of the control standard is to determine the upper and lower limits of ICR, the upper limit of ICR is used to control the pulse pileup, and the lower limit of ICR is used to ensure that each sub-detector has a sufficient number of incident photons to ensure the signal-to-noise ratio. The pulse pileup level can be evaluated by DLR, which is defined as:

$$DLR = \frac{ICR - OCR}{ICR} \tag{14}$$

The relationship between DLR and ICR can be obtained by combining formula (14) with formula (12). The relationship between DLR and ICR is expressed as:

$$DLR = \frac{ICR * T_D}{1 + ICR * T_D} \tag{15}$$

To control the pulse pileup, it is required that $DLR \leq DLR_0$, where $DLR_0$ can be determined as needed (e.g. 10%, 30% ... ). For the lower limit of ICR, the number of incident photons of each sub-detector can be required to be greater than or equal to $N_0$, that is, $ICR[j]*T_{view} \geq N_0$, where $T_{view}$ denotes the exposure duration of each view. Therefore, the control standard of upper and lower limits of ICR is expressed as:

$$\frac{N_0}{T_{view}} = ICR_{min} \leq ICR_{pixel} \leq ICR_{max} = \frac{DLR_0}{T_D * (1 - DLR_0)} \tag{16}$$

In actual scanning, as many sub-detectors as possible are required to satisfy the above relationship represented by formula (16). The objective function can be constructed as:

$$f = \sum_{j=1}^{Npixel} W(ICR[j]) \tag{17}$$

where $N_{pixel}$ denotes the number of sub-detector of the photon-counting detector, and $W(ICR[j])$ can be represented as:

$$W(ICR[j]) = \begin{cases} w_0 * (ICR - ICR_{min})^2, & ICR < ICR_{min} \\ w_2 * [(ICR - ICR_{min})^2 + (ICR < ICR_{max})^2], & \\ ICR_{min} \leq ICR \leq ICR_{max} \\ w_1 * (ICR - ICR_{max})^2, & ICR > ICR_{max} \end{cases} \tag{18}$$

In formula (18), $w_0$, $w_1$, and $w_2$ respectively denote control weights. By adjusting the three weights, the relative control requirements on the number of incident photons and the pulse pileup can be adjusted. For example, $w_0 = w_1 = 0.5$ and $w_2 = 0$.

III: Real-Time Scanning Control

The scan protocol parameters, such as the scan part of the scanned object, exposure voltage V, exposure duration T for one revolution, and the number of views $N_{view}$ for each revolution of scanning. Once the exposure voltage is determined, the relationship between ECR of the radioactive source and the tube current I can be obtained from formula (1). The motion equation can be obtained based on the motion parameters. For the above-mentioned tomography scanning, the motion equation represents a relationship between a rotation angle of the radioactive source and the current exposure moment. The motion equation is expressed as:

$$\phi(t) = \phi_0 + \frac{2 * \pi * t}{T} \tag{19}$$

where $\varphi_0$ denotes the initial position of the radioactive source, T denotes the exposure duration for each revolution of scanning, and t denotes the current exposure moment. Based on the above formula (19), the position of the radioactive source at the current exposure moment can be determined, such that the current view can be determined.

Location scanning (scout scanning) is performed on the scanned object to determine the scan position and scan range. Through the location scanning, the size of the scanned object can be determined. For example, the equivalent semi-major axis and minor axis of the scanned object can be estimated to be $a_1$ and $b_1$, respectively. Then, the standard geometric model is scaled to obtain an equivalent geometric model. Further, the attenuation length of the radioactive ray from the radioactive source to the j-th sub-detector under the angle of the radioactive source for the i-th view.

The optimal exposure current is obtained based on the equivalent geometric model, the response relationship, the objective function and the motion equation. For the i-th view, the relationship between the $ICR_{ij}$ of the j-th sub-detector and the exposure current $I_i$ can be expressed as formula (20):

$$ICR_{ij} = I_i * ECR_0(V) * e^{-\mu * L_{ij}} \tag{20}$$

Based on formulas (20) and (17), the optimal exposure current for the i-th view can be obtained, $1 \leq i \leq N_{view}$. From the first view to $N_{view}$-th view during one revolution, the optimal exposure current for each view is used to complete the scanning.

From the above examples, the number of photons incident on the sub-detector can be controlled in real time based on the change in the view position and the view angle, and the pulse pileup of the photon-counting detector can be controlled at an optimal level for each view. At the same time, the signal-to-noise ratio can be flexibly adjusted.

The implementations of the present disclosure are not only applicable to tomography scanning, but also to spiral scanning. The photon-counting detectors are not limited to Non-paralyzable photon-counting detectors, and each response relationship can be determined based on actual measurement, simulation, theoretical estimation, etc.

Based on the above method implementations, the present disclosure also provides an electronic device, which will be described below with reference to the drawings.

Figure 5:
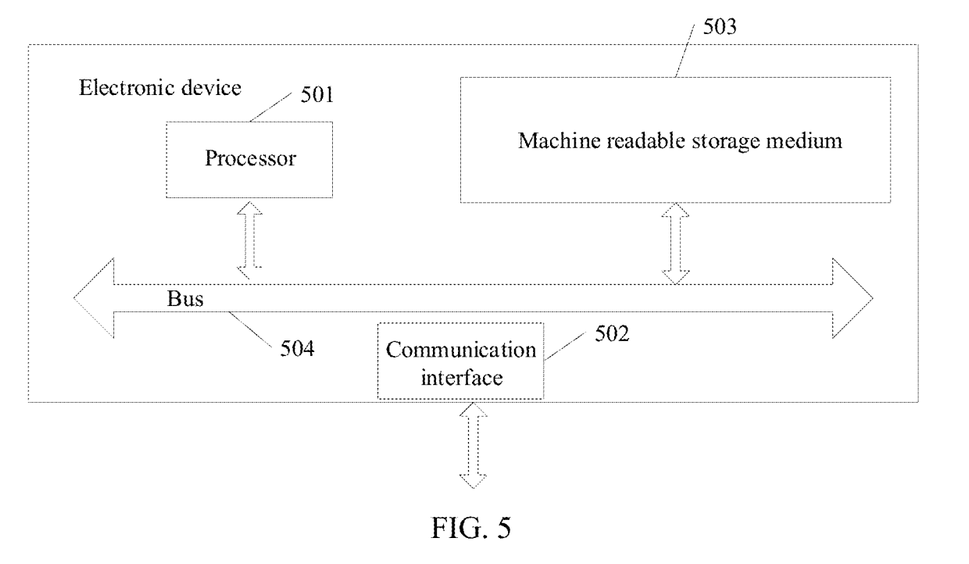
FIG. 5 is a structural diagram of an electronic device for controlling pulse pileup according to one or more examples of the present disclosure.

FIG. 5 is a schematic structural diagram of an electronic device according to one or more examples of the present disclosure. The above methods of controlling pulse pileup can be performed by the electronic device shown in FIG. 5. The electronic device shown in FIG. 5 includes a processor 501, a communication interface 502, a machine-readable storage medium 503, and a bus 504. The processor 501, the communication interface 502, and the machine-readable storage medium 503 communicate with each other via the bus 504. The electronic device shown in FIG. 5 can communicate with the CT device shown in FIG. 1 through the communication interface 502.

The machine-readable storage medium 503 can store logic instructions for controlling pulse pileup. The machine-readable storage medium can be a non-transitory memory, for example. The processor 501 can invoke and execute logic instructions in the machine-readable storage medium 503 to perform the method of controlling pulse pileup as described above. As an implementation, the logic instructions for controlling the pulse pileup can be a program for a control software. When the processor executes the instructions, the electronic device can correspondingly display the function interface for the instructions on the display interface.

The above implementations are only used to illustrate the technical solutions of the present disclosure, but not to limit them; although the present disclosure has been described in detail with reference to the foregoing implementations, those of ordinary skill in the art should understand that: the recorded technical solutions may be modified, or some of the technical features may be equivalently replaced. These modifications or replacements do not make the essence of the corresponding technical solutions deviate from the spirit and scope of the technical solutions of the implementations of the present disclosure.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure can be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, can make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other implementations are within the scope of the following claims.

What is claimed is:

1. A method of controlling pulse pileup, comprising:
    obtaining scan protocol parameters of a computed tomography (CT) device, the scan protocol parameters including an exposure voltage, an exposure duration for each revolution of a scanning of an object, and a number of views for each revolution of the scanning;
    determining an angle of a radioactive source of the CT device for an i-th view based on the number of views for each revolution of the scanning and an initial position of the radioactive source, wherein i is a positive integer among a range from 1 to the number of views for each revolution of the scanning;
    by minimizing an output value of an objective function for the i-th view, obtaining an optimal exposure current for the i-th view under the exposure voltage, wherein the output value of the objective function for the i-th view is determined based on an incident photon count rate (ICR) of each sub-detector of a photon-counting detector for the i-th view, an upper limit of ICR, and a lower limit of ICR, and wherein the ICR of the sub-detector for the i-th view is determined based on the exposure voltage, the exposure current, an attenuation coefficient of the object, and a path length for the i-th view, the path length for the i-th view being an attenuation length of a radioactive ray travelling from the radioactive source to the sub-detector and passing through the object under the angle of the radioactive source for the i-th view; and
    determining a current view based on the exposure duration for each revolution of the scanning and a current exposure moment to perform the scanning on the object with the optimal exposure current for the current view.

2. The method of claim 1, further comprising:
    establishing a standard geometric model of the object, the standard geometric model being an ellipse model; and
    determining the attenuation length of the radioactive ray travelling from the radioactive source to the sub-detector and passing through the standard geometric model under the angle of the radioactive source for the i-th view to be the path length.

3. The method of claim 2, comprising:
    before obtaining the optimal exposure current for the i-th view under the exposure voltage, performing location scanning on the object to determine a size of the object;
    scaling, based on the size of the object, the standard geometric model to obtain an equivalent geometric model of the object; and
    determining the attenuation length of the radioactive ray travelling from the radioactive source to the sub-detector and passing through the equivalent geometric model under the angle of the radioactive source for the i-th view to be the path length.

4. The method of claim 1, further comprising:
    determining the upper limit of ICR based on a maximum value of deadtime loss rate and a dead time of the photon-counting detector.

5. The method of claim 4, wherein a deadtime loss rate of the sub-detector for the i-th view is associated with the ICR of the sub-detector and an observed photon count rate (OCR) of the sub-detector for the i-th view, and
wherein the OCR of the sub-detector for the i-th view is associated with the ICR of the sub-detector for the i-th view and the dead time of the photon-counting detector.

6. The method of claim 1, further comprising:
determining the lower limit of ICR based on a minimum value of signal-to-noise ratio, an area of the sub-detector, and an exposure duration of the i-th view, wherein the exposure duration of the i-th view is obtained by dividing the exposure duration for each revolution of the scanning by the number of views for each revolution of the scanning.

7. The method of claim 6, wherein a signal-to-noise ratio of the sub-detector for the i-th view is associated with the ICR of the sub-detector for the i-th view, the area of the sub-detector, and the exposure duration of the i-th view.

8. The method of claim 1, comprising:
for each sub-detector for the i-th view, determining an increment of the output value of the objective function for the i-th view based on a relationship between the ICR of the sub-detector and the upper limit of ICR and the lower limit of ICR,
wherein, when the ICR of the sub-detector is greater than the upper limit of ICR, the output value of the objective function for the i-th view is increased from an initial output value by the increment that is based on a difference between the ICR of the sub-detector and the upper limit of ICR,
when the ICR of the sub-detector is less than the lower limit of ICR, the output value of the objective function for the i-th view is increased by the increment that is based on a difference the ICR of the sub-detector and the lower limit of ICR, and
when the ICR of the sub-detector is between the lower limit of ICR and the upper limit of ICR, the increment of the output value of the objective function is substantially identical to zero or within a predetermined range, the increment being based on a difference the ICR of the sub-detector and the upper limit of ICR and the lower limit of ICR.

9. The method of claim 1, wherein determining the optimal exposure current for the i-th view under the exposure voltage comprises:
determining, based on the exposure voltage and a plurality of exposure currents, a plurality of sets of ICR for the i-th view, each of the plurality of sets of ICR including a respective ICR of each sub-detector under a respective exposure current corresponding to the set of ICR;
for each of the plurality of sets of ICR, obtaining an output value of the objective function for the set of ICR based on the respective ICR of each sub-detector in the set of ICR, the lower limit of ICR, and the upper limit of ICR;
identifying a minimum output value of the objective function from the obtained output values of the objective function for the plurality of sets of ICR; and
determining an exposure current for the minimum output value of the objective function as the optimal exposure current for the i-th view under the exposure voltage.

10. The method of claim 1, wherein the photon-counting detector comprises a Non-paralyzable photon-counting detector.

11. A device comprising:
at least one processor; and
at least one non-transitory machine readable storage medium coupled to the at least one processor having machine-executable instructions stored thereon that, when executed by the at least one processor, cause the at least one processor to perform operations comprising:
obtaining scan protocol parameters of a computed tomography (CT) device, the scan protocol parameters including an exposure voltage, an exposure duration for each revolution of a scanning of an object, and a number of views for each revolution of the scanning;
determining an angle of a radioactive source of the CT device for an i-th view based on the number of views for each revolution of the scanning and an initial position of the radioactive source, wherein i is a positive integer in a range from 1 to the number of views for each revolution of the scanning;
by minimizing an output value of an objective function for the i-th view, obtaining an optimal exposure current for the i-th view under the exposure voltage, wherein the output value of the objective function for the i-th view is determined based on an incident photon count rate (ICR) of each sub-detector of a photon-counting detector for the i-th view, an upper limit of ICR, and a lower limit of ICR, and wherein the ICR of the sub-detector for the i-th view is determined by the exposure voltage, the exposure current, an attenuation coefficient of the object, and a path length for the i-th view, the path length for the i-th view being an attenuation length of a radioactive ray travelling from the radioactive source to the sub-detector and passing through the object under the angle of the radioactive source for the i-th view; and
determining a current view based on the exposure duration for each revolution of the scanning and a current exposure moment to perform the scanning on the object with the optimal exposure current for the current view.

12. The device of claim 11, wherein the operations further comprise:
establishing a standard geometric model of the object, the standard geometric model being an ellipse model; and
determining the attenuation length of the radioactive ray travelling from the radioactive source to the sub-detector and passing through the standard geometric model under the angle of the radioactive source for the i-th view to be the path length.

13. The device of claim 12, wherein the operations comprise:
before obtaining the optimal exposure current for the i-th view under the exposure voltage, performing location scanning on the object to determine a size of the object;
scaling, based on the size of the object, the standard geometric model to obtain an equivalent geometric model of the object; and
determining the attenuation length of the radioactive ray travelling from the radioactive source to the sub-detector and passing through the equivalent geometric model under the angle of the radioactive source for the i-th view to be the path length.

14. The device of claim 11, wherein the operations further comprise:
determining the upper limit of ICR based on a maximum value of deadtime loss rate and a dead time of the photon-counting detector.

15. The device of claim 14, wherein a deadtime loss rate of the sub-detector for the i-th view is associated with the ICR of the sub-detector and an observed photon count rate (OCR) of the sub-detector for the i-th view, and
    wherein the OCR of the sub-detector for the i-th view is associated with the ICR of the sub-detector for the i-th view and the dead time of the photon-counting detector.

16. The device of claim 11, wherein the operations further comprise:
    determining the lower limit of ICR based on a minimum value of signal-to-noise ratio, an area of the sub-detector, and an exposure duration of the i-th view, wherein the exposure duration of the i-th view is obtained by dividing the exposure duration for each revolution by the number of views for each revolution.

17. The device of claim 16, wherein a signal-to-noise ratio of the sub-detector for the i-th view is associated with the ICR of the sub-detector for the i-th view, the area of the sub-detector and the exposure duration of the i-th view.

18. The device of claim 11, wherein the operations comprise:
    for each sub-detector for the i-th view, determining an increment of the output value of the objective function for the i-th view based on a relationship between the ICR of the sub-detector and the upper limit of ICR and the lower limit of ICR,
    wherein, when the ICR of the sub-detector is greater than the upper limit of ICR, the output value of the objective function for the i-th view is increased from an initial output value by the increment that is based on a difference between the ICR of the sub-detector and the upper limit of ICR,
    when the ICR of the sub-detector is less than the lower limit of ICR, the output value of the objective function for the i-th view is increased by the increment that is based on a difference the ICR of the sub-detector and the lower limit of ICR, and
    when the ICR of the sub-detector is between the lower limit of ICR and the upper limit of ICR, the increment of the output value of the objective function is substantially identical to zero or within a predetermined range, the increment being based on a difference the ICR of the sub-detector and the upper limit of ICR and the lower limit of ICR.

19. The device of claim 11, wherein the operations comprise:
    determining, based on the exposure voltage and a plurality of exposure currents, a plurality of sets of ICR for the i-th view, each of the plurality of sets of ICR including an ICR of each sub-detector under a respective exposure current corresponding to the set of ICR;
    for each of the plurality of sets of ICR, obtaining, based on the ICR of each sub-detector in the set of ICR, the lower limit of ICR and the upper limit of ICR, an output value of the objective function for the set of ICR;
    identifying a minimum output value of the objective function from the obtained output values of the objective function for the plurality of sets of ICR; and
    determining an exposure current for the minimum output value of the objective function as the optimal exposure current for the i-th view under the exposure voltage.

20. The device of claim 11, wherein the photon-counting detector comprises a Non-paralyzable photon-counting detector.

* * * * *